United States Patent [19]

Wilson et al.

[11] Patent Number: 4,973,558

[45] Date of Patent: Nov. 27, 1990

[54] METHOD OF CULTURING CELLS USING HIGHLY GAS SATURATED MEDIA

[75] Inventors: John R. Wilson, St. Anthony; William A. Gaines, Jr., Burnsville; Darrell P. Page, Coon Rapids; William H. Harm, Robinsdale, all of Minn.

[73] Assignee: Endotronics, Inc., Coon Rapids, Minn.

[21] Appl. No.: 187,355

[22] Filed: Apr. 28, 1988

[51] Int. Cl.$^5$ .................... C12N 5/00; C12M 1/04
[52] U.S. Cl. .................... 435/240.242; 435/240.2; 435/240.241; 435/291; 435/313; 435/818
[58] Field of Search .............. 435/240.242, 240.2, 435/240.23, 240.241, 291, 313, 818; 210/321.79, 321.8, 321.88, 321.89

[56] References Cited

U.S. PATENT DOCUMENTS

| | | | |
|---|---|---|---|
| 3,172,235 | 3/1965 | Bjorklund | 47/1.4 |
| 3,407,120 | 10/1968 | Weiss et al. | 195/104 |
| 3,740,320 | 6/1973 | Arthur | 435/313 X |
| 3,821,087 | 6/1974 | Knazek et al. | 195/127 |
| 3,883,393 | 5/1975 | Knazek et al. | 195/1.8 |
| 4,220,725 | 9/1980 | Knazek et al. | 435/285 |
| 4,266,026 | 5/1981 | Breslau | 435/99 |
| 4,391,912 | 7/1983 | Yoshida et al. | 435/241 |
| 4,440,853 | 4/1984 | Michaels et al. | 435/182 X |
| 4,442,206 | 4/1984 | Michaels et al. | 435/68 |
| 4,514,499 | 4/1985 | Noll | 435/240 |
| 4,618,586 | 10/1986 | Walker | 435/1 |
| 4,629,686 | 12/1986 | Gruenberg | 435/1 |
| 4,650,766 | 3/1987 | Harm et al. | 435/284 |
| 4,721,562 | 1/1988 | Barnscheidt et al. | 210/221.2 X |
| 4,804,628 | 2/1989 | Cracauer et al. | 210/321.8 X |

FOREIGN PATENT DOCUMENTS 8602379  4/1986  PCT Int'l Appl. .

*Primary Examiner*—Robert J. Warden
*Assistant Examiner*—Rebekah A. Griffith
*Attorney, Agent, or Firm*—Sughrue, Mion, Zinn, Macpeak & Seas

[57] ABSTRACT

A method of culturing cells by providing a highly gassed media on a continuous basis to cells grown in a hollow fiber cartridge includes entraining the media with gas above the gas solubility level of the media. The media is then permitted to rest in a substantially quiescent state so that non-solubilized gas leaves the media. The media is then pressurized prior to delivery to the hollow fibers sufficiently so that the pressure drop and/or flow disturbance in the cell culturing device does not decrease the gas solubility level of the media below the media's gas saturation point.

8 Claims, 1 Drawing Sheet

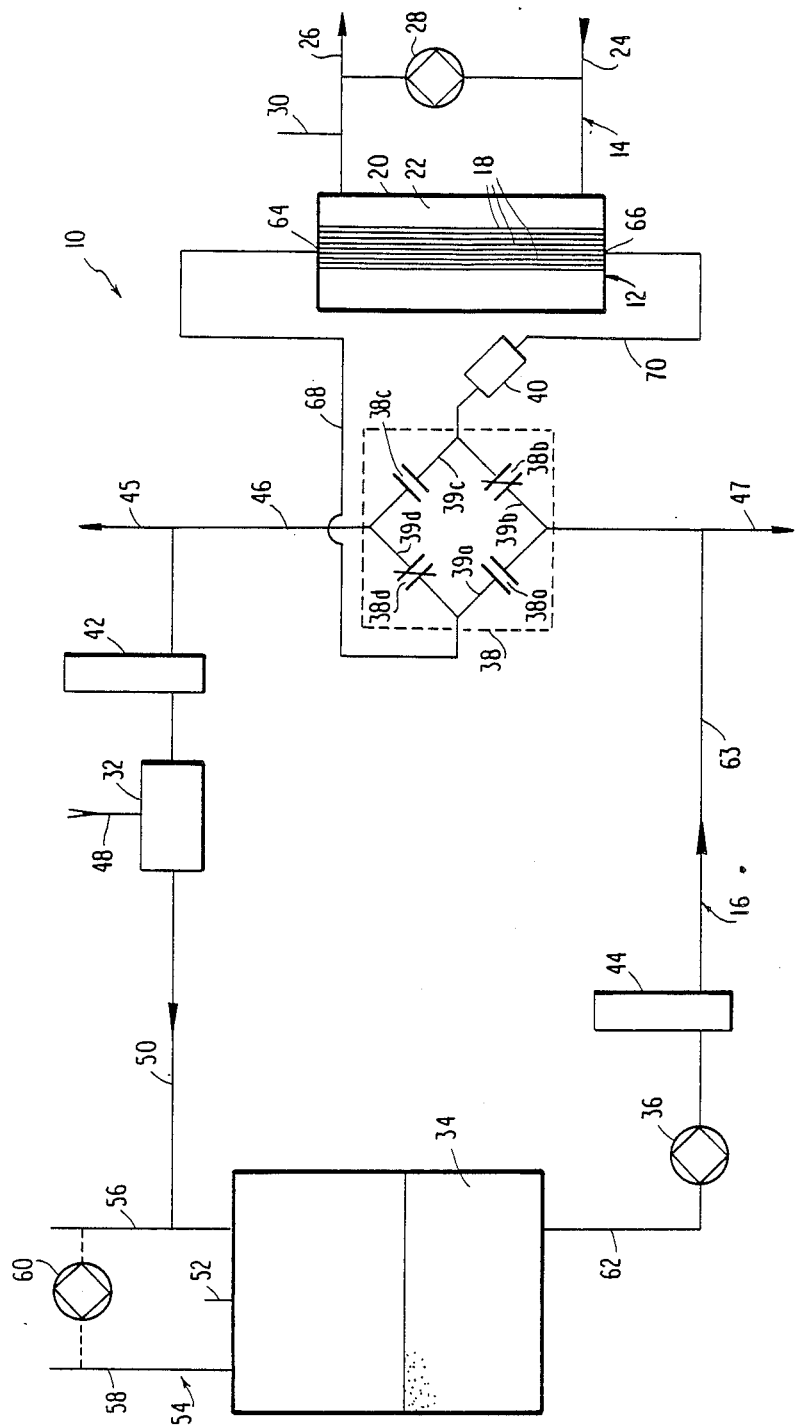

METHOD OF CULTURING CELLS USING HIGHLY GAS SATURATED MEDIA

BACKGROUND OF THE INVENTION

1. Field of the Invention

The present invention relates to a method of culturing cells in vitro, and in particular, it relates to a method of culturing cells using hollow fiber membranes.

2. Description of the Prior Art

A primary factor for optimum growth and maintenance of cells is oxygen. Various methods of oxygenating the media have been described. In the Björklund U.S. Pat. No. 3,172,235, direct oxygenation of the culturing flask is disclosed. The Michaels et al U.S. Pat. Nos. 4,440,853 and 4,442,206 describe methods of directly oxygenating the media in a reservoir. The Gruenberg U.S. Pat. No. 4,629,686 and the Walker U.S. Pat. No. 4,618,586 describe oxygenating the media in media source vessels.

On-line oxygenation of the media is described in the Weiss et al U.S. Pat. No. 3,407,120 wherein an aeration column is disclosed that oxygenates the media prior to the media being delivered to the cell culturing device. The Knazek et al U.S. Pat. Nos. 3,821,087, 3,883,393, and 4,220,725 describe the use of an oxygenator or artificial lung having a silicone rubber membrane to provide gas transfer for perfusing the media. The Yoshida et al U.S. Pat. No. 4,391,912 describes the use of a hollow fiber cartridge to oxygenate media.

Another method of oxygenating the media on-line is disclosed in the Harm et al U.S. Pat. No. 4,650,766 which describes the use of a gassing block for introducing gas into the media through gas-defusable tubing.

The Noll U.S. Pat. No. 4,514,499 describes a gas permeater that oxygenates the media upstream of a reservoir in a recirculation loop. A pump downstream of the reservoir provides the motive force to deliver the media into a cell culturing device.

The development of culturing cells in vitro has grown tremendously in recent years. One method of cell culturing includes the use of hollow fiber cartridges wherein media is continously transported through the lumen of the hollow fibers while cells are being cultured in an extracapillary space between the hollow fibers and the shell of the hollow fiber cartridge.

In the continuous culturing of cells using hollow fiber cartridges, problems occur in using a highly oxygenated media, that is a media oxygenated near its oxygen saturation level. As the media traverses the wall of the lumen a pressure drop occurs, lowering the oxygen solubility level of the media. This phenomena results in oxygen leaving solution in the extracapillary space. The oxygen then occupies areas within the cell culturing area of the hollow fiber cartridge reducing the space available for the cells to grow.

SUMMARY OF THE INVENTION

The present invention includes a method of culturing cells in hollow fiber cartridges using a highly gassed media. The method includes entraining the media with a gas such as air so that the media is saturated past the media's gas solubility level. The media is then permitted to rest in a substantially quiescent state so that non-solubilized air leaves the media. After the excess air leaves the media, the media is pressurized so that the air solubility level of the media is increased and the media is then delivered to the hollow fibers.

Additionally, the method of the present invention includes reversing the flow of the media through the hollow fibers at selected intervals. Reversing the flow of the media through the hollow fibers changes the direction of the flow in the cell culturing space disrupting and changing concentration gradients of air, nutrients and waste to effect better maintenance of the cell culture.

BRIEF DESCRIPTION OF THE DRAWINGS

The figure is a schematic diagram of an apparatus used with the method of the present invention.

DETAILED DESCRIPTION OF THE PREFERRED EMBODIMENTS

The method of the present invention provides a highly gassed media to hollow fibers for cells being maintained and cultured exterior of the hollow fibers. The media is initially entrained with gas past the gas solubility level of the media. After gassing, the media is permitted to rest, for example, in a reservoir, in a substantially quiescent state so that gas not in solution leaves the media. Media is drawn from the reservoir and pressurized, increasing the gas solubility level of the media and delivered in a pressurized state to the hollow fibers.

The process of the present invention is practiced by using a cell culturing apparatus, generally indicated at 10 in the figure. Although a specific cell culturing apparatus is illustrated, it will be understood that other configurations are within the scope of the present invention.

The cell culturing apparatus includes a hollow fiber cartridge 12, an extracapillary space loop 14 and a media circulation loop 16.

The hollow fiber cartridge 12 includes a plurality of hollow fibers (capillaries) 18 extending longitudinally within a shell 20. Cells are cultured in the space between the exterior surfaces of the hollow fibers 18 and the interior surface of the shell 20 and will be referred to as the extracapillary space 22. The hollow fibers have, selectively permeable wall membranes that allow solubilized factors such as oxygen, $CO_2$, nutrients and other chemical components to diffuse through the walls into the extracapillary space 22 and to allow waste such as lactic acid to diffuse back into the lumen of the fibers.

An inlet conduit 24 is in fluid communication with the extracapillary space and provides access and a means for delivering factors into the extracapillary space. An outlet conduit 26 provides a passageway out of the extracapillary space 22.

A multiple output pump 28, such as a peristaltic pump, provides motive force for introducing fluid into the extracapillary space and for delivering factors and other nutrients to the cells being maintained therein. In addition, the pump 28 is used for harvesting products produced by the cells. The extracapillary space may be sampled or inoculated through an access line 30.

The circulation of media through the extracapillary space is described in International Application PCT/U.S. Pat. No. 85/01948, published on Apr. 24, 1986, claiming priority from U.S. application Ser. No. 658,549 now abandoned, assigned to the same assignee as the present application entitled "HOLLOW FIBER CELL CULTURE DEVICE AND METHOD OF OPERATION", filed on Oct. 9, 1984, and which is herein incorporated by reference.

The media circulation loop 16 includes a jet pump 32, a reservoir 34, and a media circulation pump 36 as primary components. The loop 16 circulates media from the reservoir to the hollow fiber cartridge on a continuous basis. Additionally, a switching mechanism 38 permits flow to the hollow fibers to be reversed at selected time intervals. Secondary components of the media circulation loop include a temperature sensor 40, a dissolved oxygen probe 42 and a pH probe 44. One sample line 45 is provided downstream of the cartridge 12 and another sample line 47 is provided upstream of the cartridge 12.

The media circulation loop 16 provides gassed media that does not "outgas" in the cell culturing device. By "outgas" is meant the phenomena of gas leaving solution due to a decrease in the gas solubility level of the media. Outgassing in the extracapillary space occurs when fluid carrying the gas in solution traverses the lumen wall into the extracapillary space, thus experiencing a pressure drop which causes a lowering of the solubility point. A portion of the gas previously maintained in solution is released into the extracapillary space thereby occupying volume that would otherwise be occupied by cells. Cells cannot grow in a space solely occupied by a gas, and therefore "outgassing" is deleterious to efficient cell growth in a hollow fiber cartridge.

As media exits the lumen of the hollow fiber through conduit 46, the media is gassed by jet pump 32. Jet pumps are well known and described in "Applied Fluid Dynamics Handbook", by Robert D. Blevins, published by Van Nostrand Reinhold Company, 1984. The jet pump 32 is a device that permits entrainment of one fluid into the other. In the present invention, the jet pump 32 is used to entrain gas such as air from a source represented by line 48. Air is entrained to oxygenate the media. Other gases such as $CO_2$ can also be introduced in the same manner. The gas is entrained into the media and mixed at a level in excess of the gas solubility level of the media. By gas solubility level is meant a level at which the media no longer forms a homogenous solution with the gas. When media no longer forms a homogenous solution, the media has reached its gas saturation point. The amount of gas entrained is such that an excess of gas not in solution with the media exists.

The gas entrained media is delivered into the reservoir 34 through conduit 50. The media is permitted to rest in a substantially quiescent state in the reservoir 34 to permit the gas not in solution to rise and leave the media. The reservoir 34 includes a vent represented by line 52 for venting gas entrained in the media which includes excess gas introduced by the jet pump as well as waste gas produced by the cells.

A media delivery system 54 includes an inlet line 56 and an outlet line 58 and a multiple output pump 60 such as a peristaltic pump for initially filling the reservoir with fresh media and for adding and removing media from the reservoir when needed.

The oxygen saturated media is drawn from the reservoir 34 through conduit 62 by the pump 36. The pump 36 is a positive displacement pump such as a peristaltic pump. The pump 36 has a three-fold purpose. First, the pump delivers media from the reservoir 34 to the hollow fibers 18 and circulates media through the loop 16. Second, the pump of the present invention is located in a manner so that the media is placed under sufficient pressure to increase the gas solubility level of the media. Third, the pump collapses any gas bubbles that have not been removed in the reservoir, thus driving the gas into solution and thereby further increasing the solubilized gas level of the media. The pump preferably pumps the media at a constant rate.

The media entering the pump 36 is at its gas saturation point with the majority of non-solubilized gas having been removed in the reservoir. The media exiting the pump is no longer at a gas saturation point due to the increase in pressure which results in an increase in the gas solubility level. Increasing the gas solubility level of the media allows unremoved gas bubbles to enter solution as well as creating a margin between the actual soluable level and the solubility limit which allows fluctuation in the solubility limit without outgassing. The amount that the gas solubility level is increased is primarily a function of the downstream back pressure caused by the jet pump. In one working embodiment, media pressurized to 10 psig as measured at the outlet of pump 36 was sufficient to prevent outgassing in the hollow fiber cartridge. The hollow fibers were made of regenerated cellulose with 5,070 hollow fibers in the cartridge. The fibers have an inner diameter of 200 $\mu$m and an outer diameter of 220 $\mu$m with the fiber length being approximately 230 mm.

The switching mechanism 38 provides for media entry into the hollow fiber cartridge through end 64 or end 66. The switching mechanism 38 is preferably made of flexible tubing sections 39a, 39b, 39c, and 39d, all in fluid communication. The sections 39a, 39b, 39c, and 39d include pinch sections 38a, 38b, 38c and 38d, respectively. Tubing sections 38a and 38b act as alternative inlets to the switching mechanism and are in fluid communication with conduit 63 which is connected to the outlet of the pump 36. Tubing sections 38d and 38c act as alternative outlets of the switching mechanism and are both in fluid communication with the tubing 46.

The tubing sections 38a and 38c are disposed such that a first pinch clamp will pinch tubing sections 38a and 38c simultaneously while tubing sections 38b and 38d are left unrestricted. Similarily, tubing sections 38b and 38d are disposed such that a second pinch clamp restricts flow in tubing sections 38b and 38d simultaneously while 38a and 38c are left unrestricted.

To enable media to enter the hollow fiber cartridge 12 at end 64, pinch sections 38b and 38d are pinched or restricted while pinch sections 38a and 38c are unrestricted. The media then flows through tubing section 39a and into tubing section 68 into the culturing device 12 at end 64. The media exits the device 12 at end 66 and flows through tubing 70, through tubing section 39c and into tubing 46.

To provide flow into the cell culturing device at end 66, tubing pinch sections 38a and 38c are pinched while pinch sections 38b and 38d are left unrestricted. The media then flows through tubing section 39b and into the tubing section 70 and into the cell culturing device 12 at end 66. The media exits at end 64 and flows through tubing 68 and through tubing section 39d and into tubing 46.

Reversing the flow of the media in the hollow fibers disrupts the concentration gradients of oxygen, nutrients and waste that have developed in the hollow fiber cartridge. When the flow enters the hollow fiber cartridge at end 64, oxygen and nutrient concentration will be greater at end 64 decreasing across the length of the hollow fiber cartridge while lactic acid concentration increases toward end 66. Switching the flow so that media enters the hollow fiber cartridge at end 66, reverses the concentration gradient within the extracapillary space 22 so that oxygen and nutrient concentrations are greater toward end 66 decreasing across the length of the hollow fibers and lactic acid concentration increasing toward the end 64.

The process of the present invention also permits measurement of oxygen usage by the cells being cultured in the cell culturing device. Dissolved oxygen measurements are taken by dissolved oxygen probe 42 which is downstream of the cell culturing device. Meaningful data of oxygen usage could not be obtained in prior art cell culturing system that entrained media with gas bubbles since the non-solubilized oxygen would function as a source of oxygen keeping the oxygen level always at the saturation point. Using the process of the present invention, oxygen usage by the cells can be monitored since outgassing does not occur.

Although the present invention has been described with reference to preferred embodiments, workers skilled in the art will recognize that changes may be made in form and detail without departing from the spirit and scope of the invention.

What is claimed is:

1. A method of culturing cells comprising:
    supplying a gassed media on a continuous basis to a cell culturing device wherein the media is passed through hollow fibers and the cells are cultured in a space exterior of the hollow fibers;
    entraining the media with gas past the gas solubility level of the media;
    permitting the media to rest in a substantially quiescent state so that non-solubilized gas leaves the media;
    pressurizing the media so that the gas solubility level of the media increases to a level such that a pressure drop through the cell culturing device does not decrease the gas solubility level of the media below the gas saturation point of the media; and
    delivering the pressurized media to the hollow fibers.

2. The method of claim 1 and further including:
    reversing the flow of media through the hollow fibers at selected time intervals.

3. The method of claim 1 and further including
    the step of: monitoring oxygen consumption by the cells by monitoring oxygen levels downstream of the cell culturing device.

4. The method of claim 1 wherein the method comprises pressurizing the media using a positive displacement pump.

5. The method of claim 4 wherein the method comprises delivering the media by pumping the media at a constant rate.

6. The method of claim 1 wherein the method comprises entraining the media with gas using a jet pump.

7. The method of claim 6 wherein the method comprises mixing the media and gas downstream of the cell culturing device.

8. The method of claim 6 wherein the gas is air.

* * * * *